United States Patent [19]

Clerici et al.

[11] Patent Number: 4,895,988

[45] Date of Patent: Jan. 23, 1990

[54] PROCESS FOR THE MUTUAL CONDENSATION OF AROMATIC AND CARBONYLIC COMPOUNDS

[75] Inventors: Mario G. Clerici, Milan; Giuseppe Bellussi, Piacenza, both of Italy

[73] Assignees: Eniricerche S.p.A., Milan; Enichem Sythesis S.p.A., Palermo; Snamprogetti S.p.A., Milan, all of Italy

[21] Appl. No.: 110,329

[22] Filed: Oct. 20, 1987

[30] Foreign Application Priority Data

Oct. 22, 1986 [IT] Italy ............................. 22073 A/86

[51] Int. Cl.$^4$ ...................... C07C 37/20; C07C 39/12
[52] U.S. Cl. ................................. 568/727; 568/722; 568/728
[58] Field of Search ............................. 568/727, 728

[56] References Cited

U.S. PATENT DOCUMENTS

| | | | |
|---|---|---|---|
| 3,496,239 | 2/1970 | Hamilton et al. | 568/727 |
| 3,728,408 | 4/1973 | Tobias | 568/727 |
| 4,317,944 | 3/1982 | Davis | 568/727 |
| 4,694,111 | 9/1987 | Gupta | 568/727 |

*Primary Examiner*—Werren B. Lone
*Attorney, Agent, or Firm*—Hedman, Gibson, Costigan & Hoare

[57] ABSTRACT

The mutual condensation of aromatic and carbonylic compounds is carried out with zeolitic materials derived from silicalite by replacing a portion of silicon with B and Al, Al and Ti, Ti and Fe, and with ZSM-5, to yield diaryl-alkanes.

20 Claims, No Drawings

PROCESS FOR THE MUTUAL CONDENSATION OF AROMATIC AND CARBONYLIC COMPOUNDS

A general method of synthesis of diaryl-alkanes is based on the condensation of one mole of a carbonylic compound with 2 moles of aromatic compounds. Catalysts efficacious in this reaction are both organic and inorganic acids, and, sometimes, bases. However, it is necessary to operate under carefully controlled conditions, in order to avoid the formation of large amounts of byproducts. In fact, the carbonylic compounds are very reactive, so that it is difficult to prevent the diaryl-alkane from further reacting yielding higher oligomers and polymeric compounds. In the relevant technical literature (J. Cat. 6, 237, 1966), also the use of zeolitic catalysts (X, Y, mordenites) in the acidic form, or exchanged with metals belonging to the lanthanide group is described.

But they result active at rather high temperatures, and furthermore undergo rather fast deactivation processes, due to the formation in the cages of high-molecular weight compounds.

The present Applicant has surprisingly found now that zeolitic materials which can be derived from silicalite by replacing a portion of silicon with B and Al, Al and Ti, Ti and Fe are catalysts efficacious in the synthesis of the diaryl-alkanes. Also ZSM-5 can be used for this process, even if it leads to lower yields. In fact, they show a high catalytic activity in the mutual condensation of the aromatic molecule and the carbonylic molecule, whilst their particular structure (channels of approximately 6 Å of diameter) discourages the further growth of the diaryl-alkane towards higher-molecular-weight condensation products.

Relatively to the catalysts described in the technical literature (J. Cat. 6, 237, 1966), the catalysts used according to the present invention have a higher activity, and are less prone to be deactivated.

Even if it is not strictly necessary, it is preferable to run the reaction in a suitable inert solvent, above all at high conversions. Said solvent must be able to dissolve the reactants used: for example, a polar solvent (such as water) in case of formaldehyde and phenol; and benzene, in case of trioxane and phenol.

The reaction temperature can vary within the range of from room temperature to 200° C., preferably of from 50° to 120° C.

The reaction can be carried out both batchwise and continuously, separating the reaction product leaving the reactor, and recycling the unconverted reactants.

As to the nature of the diaryl-alkane formed, the various possible isomers can be present, with a marked prevalence of the lowest-hindrance isomer, as shown by the following reaction scheme:

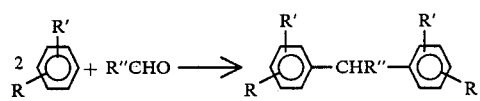

wherein:

R, R′ = hydrogen, hydroxyl, alkoxy, and halogen; and

R″ = hydrogen and either substituted or non-substituted alkyl or aryl.

The reaction pressure is the autogenous pressure.

The zeolites which are used in the process according to the present invention are those which meet the following general formula, expressed as the molar ratios of the oxides (in the calcined and anhydrous form):

$$pHAlO_2.qB_2O_3.SiO_2 \quad (1)$$

wherein p has a value comprised within the range of from 0.034 to 0.0050, and g has a value comprised within the range of from 0.1 to 0.005, and the $H^+$ of $HAlO_2$ can be at least partially replaced by cations, wherein the zeolite of formula (1) has a powder X-ray diffraction spectrum, whose meaningful lines are reported in Table A.

TABLE A

| d | $I_{rel}$ |
|---|---|
| 11.12 + 0.10 | vs |
| 9.98 + 0.10 | s |
| 9.74 + 0.10 | m |
| 6.34 + 0.07 | mw |
| 5.97 + 0.07 | mw |
| 4.24 + 0.05 | mw |
| 3.84 + 0.04 | s |
| 3.81 + 0.04 | s |
| 3.73 + 0.04 | s |
| 3.71 + 0.04 | s |
| 3.63 + 0.04 | m |
| 3.04 + 0.02 | mw |
| 2.97 + 0.02 | mw | wherein d are the interplanar distances, as Å, and $I_{rel}$ are the relative intensities, wherein vs means very strong; s = strong; m = medium; mw = medium-weak; w = weak; and an I.R. spectrum at least showing the following bands:

| wn | $I_{rel}$ |
|---|---|
| 1220–1230 | w |
| 1080–1110 | s |
| 890–920 | mw |
| 795–805 | mw |
| 550–560 | m |
| 450–470 | ms | wherein wn is the wave number, as $cm^{-1}$ and $I_{rel}$ are the relative intensities, wherein s means strong; ms = medium-strong; m = medium; mw = medium-weak; w = weak.

$$pHAlO_2.qTiO_2.SiO_2 \quad (2)$$

wherein p has a value larger than zero and smaller than, or equal to 0.050, and g has a value larger than zero and smaller than or equal to 0.025; and the $H^+$ of $HALO_2$ can be at least partially replaceable, or replaced, by cations, wherein the zeolite having the general formula (2) has a X-ray diffraction spectrum of the powders, whose meaningful lines are reported in following Table B.

TABLE B

| d | $I_{rel}$ |
|---|---|
| 11.14 + 0.10 | vs |
| 9.99 + 0.10 | s |
| 9.74 + 0.10 | m |
| 6.36 + 0.07 | mw |
| 5.99 + 0.07 | mw |
| 4.26 + 0.05 | mw |
| 3.86 + 0.04 | s |
| 3.82 + 0.04 | s |
| 3.75 + 0.04 | s |

TABLE B-continued

| d | $I_{rel}$ |
|---|---|
| 3.72 + 0.04 | s |
| 3.65 + 0.04 | m |
| 3.05 + 0.02 | mw |
| 2.99 + 0.02 | mw | wherein d are the interplanar distances, as Å, and $I_{rel}$ are the relative intensities, wherein vs means very strong; s=strong; m=medium; mw=medium-weak; w=weak; and the zeolite having the general formula (2) shows an I.R. spectrum at least showing the following bands:

| wn | $I_{rel}$ |
|---|---|
| 1220–1230 | w |
| 1080–1110 | s |
| 960–975 | mw |
| 795–805 | mw |
| 550–560 | m |
| 450–470 | ms | wherein wn is the wave number, as $cm^{-1}$ and $I_{rel}$ are the relative intensities, wherein s means strong; ms=medium-strong; m=medium; mw=medium-weak; w=weak.

$$pHFeO_2 \cdot qTiO_2 \cdot SiO_2 \quad (3)$$

wherein p has a value larger than zero and smaller than, or equal to 0.050, and g has a value larger than zero and smaller than or equal to 0.025; and the $H^+$ of $HFeO_2$ can be at least partially replaceable, or replaced, by cations, wherein the zeolite having the general formula (3) has an X-ray diffraction spectrum of the powders, whose most meaningful lines are reported in Table C.

TABLE C

| d | $I_{rel}$ |
|---|---|
| 11.14 + 0.10 | vs |
| 9.99 + 0.10 | s |
| 9.74 + 0.10 | m |
| 6.36 + 0.07 | mw |
| 5.99 + 0.07 | mw |
| 4.26 + 0.05 | mw |
| 3.86 + 0.04 | s |
| 3.82 + 0.04 | s |
| 3.75 + 0.04 | s |
| 3.72 + 0.04 | s |
| 3.65 + 0.04 | m |
| 3.05 + 0.02 | mw |
| 2.99 + 0.02 | mw | wherein d are the interplanar distances, as Å, and $I_{rel}$ are the relative intensities, wherein vs means very strong; s=strong; m=medium; mw=medium-weak; w=weak, and wherein the zeolite having the general formula (3) shows and I.R. spectrum at least showing the following bands:

| wn | $I_{rel}$ |
|---|---|
| 1220–1230 | w |
| 1080–1110 | s |
| 960–975 | mw |
| 795–805 | mw |
| 550–560 | m |
| 450–470 | ms | wherein wn is the wave number, as $cm^{-1}$ and $I_{rel}$ are the relative intensities, wherein s means strong; ms=medium-strong; m=medium; mw=medium-weak; w=weak.

$$ZSM-5 \quad (4)$$

of Mobil Oil Corporation, as from U.S. Pat. No. 3,702,886 and Reissue U.S. application Ser. No. 29,948.

Zeolites 1, 2, 3 and 4 are prepared by means of the following procedures:

Zeolite 1:

Under hydrothermal conditions a silicon derivative, a boron derivative, and aluminum derivative and a nitrogenous organic base are reacted, with an $SiO_2/Al_2O_3$ molar ratio of the reactants larger than 100, preferably comprised within the range of from 300 to 400, an $SiO_2/B_2O_3$ molar ratio of the reactants comprised within the range of from 5 to 50, an $H_2O/SiO_2$ molar ratio of the reactants preferably comprised within the range of from 20 to 40, possibly in the presence of one or more alkali-and or alkali-earth-metal salts and/or hydroxides, with a molar $M/SiO_2$ ratio (wherein M is the alkali- and/or alkali-earth-metal cation) of the reactants smaller than 0.1, preferably smaller than 0.01, or equal to zero.

In the empirical formula of the material, aluminum has been shown in $HAlO_2$ form, to underline that the material is in $H^+$ form. When the ratios between the various reactants are discussed, for aluminum the $Al_2O_3$ form is used, in that it is the most usual.

The silicon derivative is selected from silica gel, silica sol and alkyl-silicates, among which tetraethylsilicate is the most preferred; the boron derivative is selected from boric acid and the organic derivatives of boron, such as, e.g., alkyl-borates, preferably triethylborate; the aluminum derivative is selected from its salts, such as, e.g., the halides and the hydroxides, and its organic derivatives, such as, e.g., the alkyl aluminates, preferably isopropyl-aluminate.

The nitrogenous organic base can be an alkylammonium hydroxide, preferably tetrapropyl-ammonium hydroxide.

In case tetrapropyl-ammonium hydroxide is used, the $TPA^+/SiO_2$ ratio (wherein TPA=tetrapropyl-ammonium) of the reactants is comprised within the range of from 0.1 to 1, preferably of from 0.2 to 0.4.

The reactants are reacted by operating at a temperature comprised within the range of from 100° to 200° C., preferably comprised within the range of from 160° to 180° C., at a pH comprised within the range of from 9 to 14, preferably of from 10 to 12, and for a time ranging from 1 hour to 5 days, preferably of from 3 hours to 10 hours.

Zeolite 2:

Under hydrothermal conditions a silicon derivative, a titanium derivative, an aluminum derivative and a nitrogenous organic base are reacted, with an $SiO_2/Al_2O_3$ molar ratio of the reactants larger than 100, preferably comprised within the range of from 300 to 400, an $SiO_2/TiO_2$ molar ratio of the reactants larger than 5, preferably comprised within the range of from 15 to 25, an $H_2O/SiO_2$ molar ratio of the reactants preferably comprised within the range of from 10 to 100, more preferably within the range of from 30 to 50, possibly in the presence of one or more alkali- and or alkali-earth-metal salts and/or hydroxides, with a molar $M/SiO_2$ ratio (wherein M is the alkali- and/or alkali-earth-metal cation) of the reactants smaller than 0.1, preferably smaller than 0.01, or equal to zero.

In the empirical formula of the material, aluminum has been shown in the $HAlO_2$ form, to underline that the material is in $H^+$ form. When the ratios between the various reactants are discussed, for aluminum the $Al_2O_3$ form is used, in that it is the most usual.

The silicon derivative is selected from silica gel, silica sol and alkyl-silicates, among which tetraethyl-silicate is the most preferred; the titanium derivative is selected from the salts, such as, e.g., the halides, and the organic derivatives of titanium, such as, e.g., alkyl-titanates, preferably tetraethyl-titanate; the aluminum derivative is selected from its salts, such as, e.g., the halides and the hydroxides, and its organic derivatives, such as, e.g., the alkyl aluminates, preferably isopropyl-aluminate.

The nitrogenous organic base can be an alkyl-ammonium hydroxide, preferably tetrapropyl-ammonium hydroxide.

In case tetrapropyl-ammonium hydroxide is used, the $TPA^+/SiO_2$ ratio (wherein TPA=tetrapropyl-ammonium) of the reactants is comprised within the range of from 0.1 to 1, preferably of from 0.2 to 0.4.

The reactants are reacted by operating at a temperature comprised within the range of from 100° to 200° C., preferably comprised within the range of from 160° to 180° C., at a pH comprised within the range of from 9 to 14, preferably of from 10 to 12, and for a time ranging from 1 hour to 5 days, preferably of from 3 hours to 10 hours.

Zeolite 3:

Under hydrothermal conditions a silicon derivative, a titanium derivative, an iron derivative and a nitrogenous organic base are reacted, with an $SiO_2/Fe_2O_3$ molar ratio of the reactants larger than 50, preferably comprised within the range of from 150 to 600, an $SiO_2/TiO_2$ molar ratio of the reactants larger than 5, preferably comprised within the range of from 15 to 25, an $H_2O/SiO_2$ molar ratio of the reactants preferably comprised within the range of from 10 to 100, more preferably within the range of from 30 to 50, possibly in the presence of one or more alkali- and or alkali-earth-metal salts and/or hydroxides, with a molar $M/SiO_2$ ratio (wherein M is the alkali- and/or alkali-earth-metal cation) of the reactants smaller than 0.1, preferably smaller than 0.08, or equal to zero.

In the empirical formula of the material, iron has been shown in $HFeO_2$ form, to underline that the material is in $H^+$ form. When the ratios between the various reactants are discussed, for iron the $Fe_2O_3$ form is used, in that it is the most usual.

The silicon derivative is selected from silica gel, silica sol and alkyl-silicates, among which tetraethyl-silicate is the most preferred; the titanium derivative is selected from the salts, such as, e.g., the halides, and the organic derivatives of titanium, such as, e.g., alkyl-titanates, preferably tetraethyl-titanate; the iron derivative is selected from its salts, such as, e.g., the halides or the nitrates, the hydroxides, and the organic derivatives, such as, e.g., the alkoxides.

The nitrogenous organic base can be an alkyl-ammonium hydroxide, preferably tetrapropyl-ammonium hydroxide.

In case tetrapropyl-ammonium hydroxide is used, the $TPA^+/SiO_2$ ratio (wherein TPA=tetrapropyl-ammonium) of the reactants is comprised within the range of from 0.1 to 1, preferably of from 0.2 to 0.4.

The reactants are reacted by operating at a temperature comprised within the range of from 100° to 200° C., preferably comprised within the range of from 160° to 180° C., at a pH comprised within the range of from 9 to 14, preferably of from 10 to 12, and for a time ranging from 1 hour to 5 days, preferably of from 3 hours to 10 hours.

Zeolite 4:

ZSM-5; preparation as disclosed by U.S. Pat. No. 3,702,886 and Reissue U.S. application Ser. No. 29,948.

According to a second form of practical embodiment of the present invention, the zeolites 1, 2 and 3 can be in the form bonded with amorphous oligomeric silica, wherein the molar ratio of the oligomeric silica to zeolite 1, or zeolite 2, or zeolite 3 is comprised within the range of from 0.05 to 0.12, the crystals of zeolite 1, zeolite 2, zeolite 3 being encaged by Si—O—S bridges, the mass of crystals of zeolites with silica being in the form of microspheres having a diameter comprised within the range of from 5 to 1000 μm.

The process for preparing the zeolites 1, 2 and 3 with the bonding agent consists in dispersing in an aqueous solution of silica and tetraalkyl-ammonium hydroxide, wherein the alkyl radicals preferably have a number of carbon atoms comprised within the range of from 1 to 5, more preferably with tetrapropyl-ammonium, prepared by hydrolysing at a temperature comprised within the range of from room temperature to 200° C., preferably of from 40° to 100° C., in the liquid phase, a tetraalkyl-orthosilicate, preferably tetraethyl-orthosilicate, in an aqueous solution of tetraalkyl-ammonium hydroxide, for a time comprised within the range of from 0.2 to 10 hours, zeolite 1, or zeolite 2, or zeolite 3, each containing a percentage by weight of organic base comprised within the range of from 7 to 12% and a percentage of water comprised within the range of from 23 to 28%, submitting the so-obtained suspension to a fast drying.

The following Examples illustrate the specific non-limitative preparations of the zeolites used:

EXAMPLE 1

Zeolite 1

67.8 g of $AL(NO_3)_3.9H_2O$ is dissolved in 1,275 g of ethyl alcohol and to the so-obtained solution 2,819 g of tetraethyl-silicate is added, with stirring until a homogeneous and clear solution is obtained.

To a stainless-steel vessel 1,036 g of deionized water, 8,878 g of an aqueous solution at 15.5% by weight of tetrapropyl-ammonium ($TPA^+$) hydroxide and 167.5 g of boric acid powder are charged in the order shown, with stirring.

When all the acid has gone into solution, to this latter the previously obtained solution is added, and the mixture is stirred, while being heated at 60° C. for approximately 4 hours, and anyway until the hydrolysis of the silicate is complete and the ethyl alcohol present is nearly completely removed. The molar composition of the reaction mixture is the following:

$SiO_2/Al_2O_3 = 150;$
$SiO_2/B_2O_3 = 10;$
$TPA^+/SiO_2 = 0.5;$
$H_2O/SiO_2 = 35.$

The so-obtained solution is charged to an autoclave equipped with stirring means, and is heated, under its autogenous pressure, with stirring, at 170° C., for 4 hours. The discharged product is centrifuged, and the centrifuge cake is carefully dispersed in 70 liters of deionized water; the obtained suspension is centrifuged again, yielding a washed cake.

A portion of the washed centrifuge cake is calcined in air for 5 hours at 550° C., and at the end it is shown to be a zeolite having, in the anhydrous form, the following composition:

$0.0098 Al_2O_3; 0.0108 B_2O_3; SiO_2.$

EXAMPLE 2

Zeolite 1 with Bonding Agent

Zeolite 1 is prepared as disclosed in Example 1, then 219 g of tetraethyl-silicate is added, with vigorous stirring, to 234 g of solution of tetrapropyl-ammonium hydroxide at 12% by weight, and the reaction mixture is stirred for 1 hour; then 958 g of demineralized water is added to it, and stirring is continued for a further hour. A clear solution is thus obtained, inside which 875 g of the centrifuging cake prepared as above said, containing 9% by weight of TPA+, 26% by weight of water and 65% by weight of zeolite 1 are dispersed.

The milky suspension resulting from the dispersion is fed to a spray-dryer (NIRO-ATOMIZER disk-atomizer; inlet air temperature 300° C.; outlet air temperature 120° C.; chamber diameter 1.5 m), compact microspheres being obtained, which have an average diameter close to 20 μm.

The atomized product is charged to a muffle under a $N_2$ atmosphere, and is heated up to 550° C. After a 2-hour stay at that temperature under $N_2$, the atmosphere is gradually turned from $N_2$ to air, and the product is left standing a further two hours at 550° C. in air.

The obtained catalyst has the following molar composition:

$0.0088 Al_2O_3; 0.0097 B_2O_3; SiO_2.$

EXAMPLE 3

Zeolite 2

27 g of aluminum isopropoxide is dissolved in 5,400 g of solution at 18.7% by weight of tetrapropyl-ammonium hydroxide.

Separately, 230 g of tetraethyl-orthotitanate is dissolved in 4,160 g of tetraethyl-silicate, and this solution is added to the previous one, with stirring.

The resulting mixture is heated up to 50°–60° C., always with stirring, until a single-phase solution is obtained; then, 10,000 cc of water is added.

The so-obtained solution is charged to an autoclave and is heated, under its autogenous pressure, at 170° C., for 4 hours.

The product discharged from the autoclave is centrifuged and washed twice by re-dispersion and centrifugation. A portion of the washed centrifuge cake is calcined in air for 5 hours at 550° C., and at the end it shows to be a zeolite having, in the anhydrous form, the following composition:

$0.0081 Al_2O_3; 0.0250 TiO_2; SiO_2.$

EXAMPLE 4

Zeolite 2 with Bonding Agent

The zeolite is prepared as in Example 3, then 320 g of tetraethyl-silicate is added with vigorous stirring to 340 g of an aqueous solution of tetrapropyl-ammonium hydroxide at 12% by weight, and the resulting mixture is stirred 1 hour; then, 1,400 g of demineralized water is added, and the solution is kept stirred a further hour.

A clear solution is so obtained, into which 1,280 g is carefully dispersed of the washed centrifugation cake, prepared as disclosed above, containing 9% by weight of TPA+ and 26% by weight of water, and 65% of zeolite 2.

The milky suspension resulting from the dispersion is fed to a spray-dryer (NIRO-ATOMIZER disk-atomizer; inlet air temperature 300° C.; outlet air temperature 120° C.; chamber diameter 1.5 m), compact microspheres being obtained, which have an average diameter close to 20 μm.

The atomized product is charged to a muffle under a $N_2$ atmosphere and is heated up to 550° C. After a 2-hour stay at that temperature under $N_2$, the atmosphere is gradually turned from $N_2$ to air, and the product is left standing a further two hours at 550° C. in air.

The obtained product has the following molar composition:

$0.0073 Al_2O_3; 0.0225 TiO_2; SiO_2.$

EXAMPLE 5

Zeolite 3

This Example illustrates the preparation of titanium-ferrosilicalite.

20.2 g of $Fe(NO_3)_3 \cdot 9H_2O$ is dissolved in water, and from the solution the hydroxide is precipitated by means of the addition of ammonium hydrate. The precipitate is filtered off, and is washed by being re-dispersed in cold water and filtered until the filtrate turns to neutral. The damp hydroxide is then dissolved in 2,700 g of solution of tetrapropyl-ammonium hydroxide at 18.7% by weight.

Separately, 114 g of tetraethyl-orthotitanate is dissolved in 2,080 g of tetraethyl-orthosilicate, and this solution is added to the previous one, with stirring.

The resulting mixture is heated up to 50°–60° C., always with stirring, until a single-phase solution is obtained; then, 5,000 cc of water is added.

The so-obtained solution is charged to an autoclave and is heated, under its autogenous pressure, at 170° C., for 4 hours.

The product discharged from the autoclave is centrifuged and washed twice by re-dispersion and centrifugation. A portion of the washed centrifuge cake is calcined in air for 4 hours at 550° C., and at the end it shows to be a zeolite having, in the anhydrous form, the following composition:

$0.0025 Fe_2O_3; 0.0208 TiO_2; SiO_2.$

EXAMPLE 6

Zeolite 3 with Bonding Agent

The zeolite is prepared as in Example 5, then 162 g of tetraethyl-silicate is added with vigorous stirring to 173 g of a solution of tetrapropyl-ammonium hydroxide at 12% by weight, and the resulting mixture is stirred 1 hour; then, 709 g of demineralized water is added, and the solution is kept stirred a further hour.

A clear solution is so obtained, into which 720 g is carefully dispersed of the centrifugation cake, prepared as disclosed above, containing 9% by weight of TPA+ and 26% by weight of water, and 65% by weight of zeolite 3.

The milky suspension resulting from the dispersion is fed to a spray-dryer (NIRO-ATOMIZER disk-atomizer; inlet air temperature 300° C.; outlet air temperature 120° C.; chamber diameter 1.5 m), compact microspheres being obtained, which have an average diameter close to 20 μm.

The atomized product is charged to a muffle under an $N_2$ atmosphere and is heated up to 550° C. After a 2-hour stay at that temperature under $N_2$, the atmosphere is gradually turned from $N_2$ to air, and the product is left standing a further two hours at 550° C. in air.

The obtained product has the following composition:

$$0.0025Fe_2O_3; 0.0188TiO_2; SiO_2.$$

EXAMPLE 7

Zeolite 4

See U.S. Pat. No. 3,702,886 and Reissue U.S. application Ser. No. 29,948.

EXAMPLES 8-10

2 g of catalyst is suspended in a solution of 8 g of phenol, 3 g of aqueous formaldehyde (at 40%) and 50 cc of water.

With stirring, the suspension is heated at boiling temperature for 6 hours, turning gradually reddish. After removing water, the residue is extracted with ethanol, and is quantitatively analysed by gas-chromatography and mass-spectrometry by comparison with pure samples.

The results are shown in Table 1. Only trace amounts of higher oligomers are present.

TABLE 1

| Zeolite Catalyst | Phenol Conversion | Selectivity to dihydroxydiphenylmethane | | |
|---|---|---|---|---|
| | | 2,2' | 2,4' | 4,4' |
| 1 | 35% | 2.5% | 27% | 70% |
| 2 | 40% | 1.5% | 25% | 73% |
| 3 | 18% | 3.5% | 30% | 66% |

EXAMPLE 11

3 g of zeolite 2 is suspended in a mixture of 20 g of anisole and 3 cc of aqueous formaldehyde (at 40%) in 50 cc of water/ethanol at 50%. The suspension is heated in an autoclave at 120° C. for 4 hours.

Anisole conversion: 35%.
Selectivity to bis(methoxyphenyl)methane:
2,2'-isomer: 1%;
2,4'-isomer: 15%;
4,4'-isomer: 84%.

Only trace amounts of higher oligomers are present.

EXAMPLE 12

To a glass autoclave 12 g of phenol, and 1.5 g of trioxane dissolved in 60 cc of benzene are charged, together with 2 g of zeolite 1.

The reaction mixture is heated 5 hours at 120° C. with magnetic stirring. After cooling, the solvent is evaporated off, and the residue is extracted with ethanol. The reaction products are analysed and are quantitatively analysed by gas-chromatography and massspectrometry.

Phenol conversion: 65%
2,2'-dihydroxy-diphenyl-methane: 1.2 g
2,4'-dihydroxy-diphenyl-methane: 2.3 g
4,4'-dihydroxy-diphenyl-methane: 4.1 g

EXAMPLE 13

3.3 g of catalyst zeolite 2 with bonding agent is suspended in a solution of 20 g of anisole and 3 cc of aqueous formaldehyde (at 40%) in 50 cc of water/ethanol at 50%.

The suspension is heated in an autoclave at 120° C. for 4 hours.

Anisole conversion: 35%.
Selectivity to bis(methoxyphenyl)methane:
2,2'-isomer: 1%;
2,4'-isomer: 15%;
4,4'-isomer: 84%.

Only trace amounts of higher oligomers are present.

EXAMPLE 14

To a glass autoclave 12 g of phenol, 1.5 g of trioxane dissolved in 60 cc of benzene are charged, together with 2.2 g of zeolite 1 with bonding agent as the catalyst.

The reaction mixture is heated 5 hours at 120° C. with magnetic stirring. The reaction products are analysed and their amounts are determined by gas-chromatography and mass-spectrometry.

Phenol conversion: 65%
2,2'-dihydroxy-diphenyl-methane: 1.2 g
2,4'-dihydroxy-diphenyl-methane: 2.3 g
4,4'-dihydroxy-diphenyl-methane: 4.1 g

EXAMPLE 15

2.2 g of catalyst zeolite 3 with bonding agent is suspended in a solution of 8 g of phenol, 3 cc of aqueous formaldehyde (at 40%), and 50 cc of water. With stirring, the suspension is heated at the boiling temperature for 6 hours, gradually turning reddish. After removing water, the residue is extracted with ethanol and is quantitatively analysed by gas-chromatography and mass-spectrometry, by comparison with pure samples.

The results are as follows:
Phenol conversion: 18%.
Selectivity to 2,2'-dihydroxydiphenyl-methane: 3.5%
Selectivity to 2,4'-dihydroxydiphenyl-methane: 30%
Selectivity to 4,4'-dihydroxydiphenyl-methane: 66%
Only trace amounts of higher oligomers are present.

We claim:

1. A process for producing aromatic condensation products comprising: condensing an aromatic compound having the following general formula:

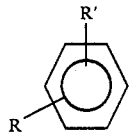

with a carbonyl compound of the general formula R″CHO to produce a diaryl-alkane of the general formula:

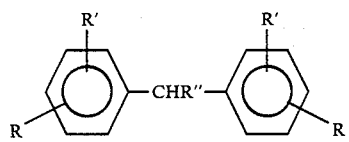

wherein:
R, R' are independently selected from the group consisting of hydrogen, hydroxyl, alkoxy, and halogen; and
R" is selected from the group consisting of hydrogen and substituted or non-substituted alkyl or aryl, wherein the reaction temperature is from about room temperature to about 200° C., and wherein the reaction is conducted in the presence of a catalyst comprising a zeolite having a pore size not greater than about 6Å in diameter.

2. The process according to claim 1, wherein the zeolite is based on a combination of elements selected from the group consisting of: (a) Si, Al and B; (b) Si, Al and Ti; (c) Si, Ti and Fe; and (d) Si and Al.

3. The process according to claim 2, wherein the zeolite based on Si, Al and B in a calcined and anhydrous form has the general formula:

$$pHAlO_2 \cdot qB_2O_3 \cdot SiO_2 \qquad (1)$$

wherein p is from 0.034 to 0.0050, and q is from 0.1 to 0.005, and the H$^+$ of HAlO$_2$ can be at least partially replaced by cations, the zeolite of formula (1) having a X-ray diffraction spectrum as reported in Table A, and an I.R. spectrum at least showing the following bands:

| wn | $I_{rel}$ |
|---|---|
| 1220–1230 | w |
| 1080–1110 | s |
| 890–920 | mw |
| 795–805 | mw |
| 550–560 | m |
| 450–470 | ms | wherein wn is the wave number, as cm$^{-1}$, and $I_{rel}$ is the relative intensity, wherein s means strong; ms means medium-strong; m means medium; mw means medium-weak; and w means weak.

4. The process according to claim 2, wherein the zeolite based on Si, Al and Ti in a calcined and anhydrous form has the general formula:

$$pHAlO_2 \cdot qTiO_2 \cdot SiO_2 \qquad (2)$$

wherein p is larger than zero and smaller than, or equal to 0.050, and q is larger than zero and smaller than or equal to 0.025, and the H$^+$ of HAlO$_2$ can be at least partially replaced, by cations, wherein the zeolite of general formula (2) has an X-ray diffraction spectrum as reported in Table B, and I.R. spectrum at least showing the following bands:

| wn | $I_{rel}$ |
|---|---|
| 1220–1230 | w |
| 1080–1110 | s |
| 960–975 | mw |
| 795–805 | mw |
| 550–560 | m |
| 450–470 | ms | wherein wn is the wave number, as cm$^{-1}$, and $I_{rel}$ is the relative intensity, wherein s means strong; ms means medium-strong; m means medium; mw means medium-weak; and w means weak.

5. The process according to claim 2, wherein the zeolite based on Si, Ti and Fe in a calcined and anhydrous form has the general formula:

$$pHFeO_2 \cdot qTiO_2 \cdot SiO_2 \qquad (3)$$

wherein p is larger than zero and smaller than, or equal to 0.050, and q is larger than zero and smaller than or equal to 0.025; and the H$^+$ of HFeO$_2$ can be at least partially replaceable by cations, wherein the zeolite of general formula (3) has an X-ray diffraction spectrum as reported in Table C, and an I.R. spectrum at least showing the following bands:

| wn | $I_{rel}$ |
|---|---|
| 1220–1230 | w |
| 1080–1110 | s |
| 960–975 | mw |
| 795–805 | mw |
| 550–560 | m |
| 450–470 | ms | wherein wn is the wave number, as cm$^{-1}$, and $I_{rel}$ is the relative intensity, wherein s means strong; ms means medium-strong; m means medium; mw means medium-weak; and w means weak.

6. The process according to claims 1, 2, 3, 4 or 5, wherein the zeolite is bonded to oligomeric silica to form microspheres, with an oligomeric silica/zeolite molar ratio of from 0.05 to 0.12, wherein the crystals of the zeolite are encaged by Si—O—Si bridges.

7. The process according to claim 6, wherein the microspheres have a diameter of from 5 to 1,000 μm.

8. The process according to claims 6 or 7 wherein the microspheres comprising oligomeric silica and the zeolite are prepared by dispersing in an aqueous solution of silica and tetraalkyl-ammonium hydroxide, prepared by hydrolyzing in the liquid phase a tetraalkyl-orthosilicate in an aqueous solution of tetraalkyl-ammonium hydroxide at a temperature of from room temperature to 200° C., and for a time of from 0.2 to 10 hours, the zeolite containing a percentage by weight of the organic base of from 7 to 12% and a percentage of water of from 23 to 28%, resulting in a suspension of the zeolite and oligomeric silica with the suspension being fast dried.

9. The process according to claim 8, wherein the tetraalkyl-orthosilicate is tetraethyl-orthosilicate.

10. The process according to claim 8, wherein the hydrolysis is carried out at a temperature of from 40° to 100° C.

11. The process according to claim 8, wherein the tetraalkyl-ammonium has alkyl radicals containing 1 to 5 carbon atoms.

12. The process according to claim 11, wherein the tetraalkyl-ammonium is tetrapropyl-ammonium.

13. The process according to claim 2, wherein the zeolite based on Si and Al is ZSM-5.

14. The process according to claim 1, wherein the reaction temperature is from room temperature to 200° C.

15. The process according to claim 2, wherein the reaction temperature is from 50° to 120° C.

16. The process according to claim 1, wherein the reaction is carried out in the presence of water, the aromatic compound is phenol, and the carbonyl compound is formaldehyde.

17. The process according to claim 1, wherein the reaction is carried out in the presence of benzene, the aromatic compound is phenol, and the carbonyl compound is trioxane.

18. The process according to claim 1, wherein the reaction is conducted under autogenous pressure.

19. The process according to claim 1, wherein the carbonyl compound is trioxane.

20. The process according to claim 1, wherein the carbonyl compound is formaldehyde.

* * * * *